(12) United States Patent
Takeuchi et al.

(10) Patent No.: US 6,579,989 B1
(45) Date of Patent: Jun. 17, 2003

(54) SULPHOSTIN ANALOGUE AND PROCESS FOR PRODUCING SULPHOSTIN AND ITS ANALOGUE

(75) Inventors: Tomio Takeuchi, Tokyo (JP); Yasuhiko Muraoka, Tokyo (JP); Masatoshi Abe, Tokyo (JP); Tetsuo Akiyama, Tokyo (JP); Shigeko Harada, Tokyo (JP)

(73) Assignee: Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 0 days.

(21) Appl. No.: 10/009,707

(22) PCT Filed: May 12, 2000

(86) PCT No.: PCT/JP00/03055

§ 371 (c)(1),
(2), (4) Date: Nov. 13, 2001

(87) PCT Pub. No.: WO00/69868

PCT Pub. Date: Nov. 23, 2000

(30) Foreign Application Priority Data

May 17, 1999 (JP) .............................. 11-135854

(51) Int. Cl.$^7$ ..................... C07D 207/46; C07D 211/92; C07D 205/085; C09F 9/553
(52) U.S. Cl. ........................ 548/412; 546/21; 540/363; 540/528
(58) Field of Search .................... 548/412; 546/21; 540/363, 528

(56) References Cited

U.S. PATENT DOCUMENTS 6,214,340 B1 * 4/2001 Takeuchi et al. ............ 424/117

FOREIGN PATENT DOCUMENTS

| EP | 0 243 924 | 11/1987 |
| GB | 830800 | 4/1957 |
| GB | 1 433 916 | 4/1976 |

OTHER PUBLICATIONS

Immunology Today, 15, p. 180–184 (Apr. 1994).

Journal of Clinical Investigation, May 1989, vol. 83, No. 5, p. 1533–1540 (1989).

Journal of Antibiotics, Apr. 1984; vol. XXXVII, No. 4, p. 422–425.

Copy of the International Search Report dated Aug. 29, 2001.

* cited by examiner

*Primary Examiner*—Charanjit S. Aulakh
(74) *Attorney, Agent, or Firm*—Nields & Lemack

(57) ABSTRACT

A sulphostin analogue represented by the general formula,

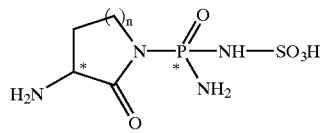

wherein n is an integer of from 0 to 3, provided that a case where n is 2 and steric configurations of C* and P* are S and R, respectively, is excluded, or a pharmaceutically acceptable salt thereof.

10 Claims, No Drawings

SULPHOSTIN ANALOGUE AND PROCESS FOR PRODUCING SULPHOSTIN AND ITS ANALOGUE

This application is a 371 of PCT/JP00/03055 filed May 12, 2000, now WO 00/69868 published Nov. 23, 2000.

TECHNICAL FIELD

The present invention relates to physiologically active substances, sulphostin and a sulphostin analogue and a process for producing the same. The compounds in accordance with the present invention possess a dipeptidylpeptidase IV inhibiting activity and are expected to be a physiologically active substance to be used, for example, as immunomodulating agents, hormone-modulating agents, anti-HIV drugs, antiallergic drugs, anti-inflammatory drugs and antirheumatic drugs.

BACKGROUND ART

Dipeptidylpeptidase IV present on the surface of T cells is known to concern itself with the activation of T cells (Immunol. Today, 15, 180–184(1994)) and is playing an important role in an immune system. In addition, the dipeptidylpeptidase IV concerns itself with the decomposition of growth-hormone-releasing hormone (J. Clin. Invest., 83, 1533–1540(1989)).

Previously, diprotin A and B and the like are known as the physiologically active substances possessing a dipeptidylpeptidase IV inhibiting activity (J. Antibiotics, 37, 422–425(1984)).

However, it cannot be said that the inhibiting activity of diprotin A and B against enzymes is sufficiently high. Therefore, a physiologically active substance possessing a higher inhibiting activity has been desired.

The present inventors previously found sulphostin as such a physiologically active substance, and developed a process for producing the same in a manner such that microorganisms which belong to Sttreptomyces and are capable of producing sulphostin of a physiologically active substance, are cultured in a medium, and the physiologically active substance, sulphostin, produced and accumulated in the cultivated substance is collected (Japanese Patent Application No. 9-317221). However, the sulphostin can exhibit a strong inhibiting activity against enzymes, yet the process of collecting it from the cultivated substance of microorganisms is not always said to be high in productivity, and the process is not suitable for mass production.

DISCLOSURE OF INVENTION

The present inventors have satisfactorily clarified a chemical structure of the physiologically active substance, sulphostin, and found that it can be obtained according to a synthetic chemical means. Further, it has been found that stereo isomers and analogues of the sulphostin, which are not naturally occurring, can be obtained similarly according to a synthetic chemical means, and can exhibit a strong enzyme inhibiting activity like the sulphostin. The present invention has been accomplished on the basis of the above-mentioned knowledge.

The present invention provides a sulphostin analogue represented by a general formula (IV') or a pharmaceutically acceptable salt thereof,

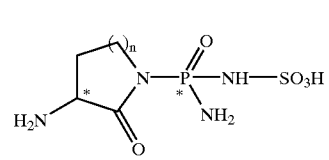

(IV')

wherein n is an integer of from 0 to 3, provided that a case where n is 2 and steric configurations of C* and P* are S and R, respectively, is excluded.

Further, the present invention provides a process for producing sulphostin or a sulphostin analogue represented by a general formula (IV),

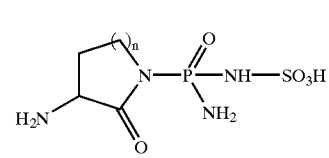

(IV)

wherein n is an integer of from 0 to 3, which comprises allowing a compound represented by a general formula (II),

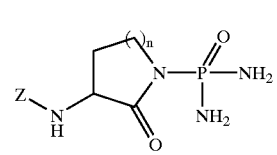

(II)

wherein n is as defined above, and Z is an amino group-protecting group, to reaction with sulfur trioxide or a complex thereof, if necessary followed by cation exchange, thereby obtaining a compound represented by a general formula (III),

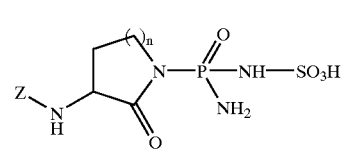

(III)

wherein n and Z are as defined above, and M is a monovalent cation, and then removing the protecting group.

Still further, the present invention provides a process for producing a compound represented by a general formula (II),

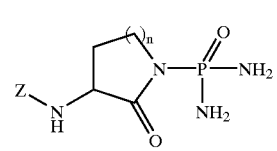

(II)

wherein n is an integer of from 0 to 3, and Z is an amino group-protecting group, which comprises allowing a compound represented by a general formula (I),

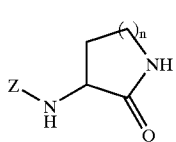

(I)

wherein n and Z are as defined above, to react with a base, followed by reaction with phosphorus oxychloride or POX₃ in which X is a halogen or imidazole, and further followed by reaction with ammonia in order.

BEST MODE FOR CARRYING OUT THE INVENTION

The present inventors have clarified that according to a variety of spectrography, the sulphostin has a chemical structure represented by the following formula (V). In addition, on the basis of a fact that L-ornithine is obtained through an experiment comprising a hydrolysis thereof, it has been also clarified that a steric configuration at a joint of the amino group is S.

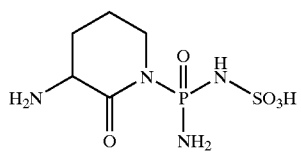

(V)

According to such a knowledge, the sulphostin has been synthesized in a manner mentioned below.

L-Ornithine is esterified, followed by ring-closure, thereby obtaining L-ornithine lactam, whose amino group is then protected in a conventional manner to obtain a compound of a general formula (VI).

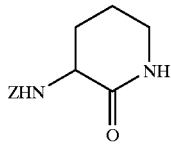

(VI)

In the formula, Z is a conventional amino group-protecting group, for example, carbamate type protecting groups such as a benzyloxycarbonyl group, whose benzyl group may be substituted with those such as a lower alkyl group, a lower alkoxy group, an acyloxy group, a nitro group and a halogen, and t-butoxycarbonyl group, amide type protecting groups such as formyl, acetyl and trifluoroacetyl, and imide type protecting groups such as phthaloyl. Preferred are carbamate type protecting groups, and more preferred is a benzyloxycarbonyl group.

Successively, the compound of the formula (VI) is treated in a non-aqueous solvent with a base, followed by reaction with POX₃ in which X is an eliminating group such as a halogen and imidazole, preferably a halogen, and further followed by reaction with ammonia, thereby obtaining a compound of a general formula (VII).

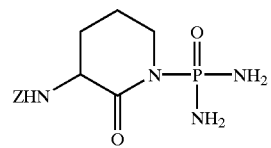

(VII)

In the formula, Z is the same amino group-protecting group as in the general formula (VI). The solvent includes an aprotic solvent, and may be anything capable of dissolving the compound of the formula (VI). Preferred is an ether solvent such as THF. The base may be anything capable of substituting hydrogen of the lactam with a metal, and includes butyllithium, sodium hydride, lithium hydride, potassium hydride, sodium bistrimethylsilylamide and lithium bistrimethylsilylamide. Preferred is butyllithium. The reaction can be carried out at a temperature of from −80 to 100° C., preferably from −80 to 0° C.

Successively, the compound of the formula (VII) is allowed to react with sulfur trioxide or a complex thereof such as a pyridine complex, a DMF complex and a trimethylamine complex, at a temperature of from 0 to 100° C., preferably from 0 to 10° C., if desired followed by cation exchange, thereby obtaining a compound of a general formula (VIII).

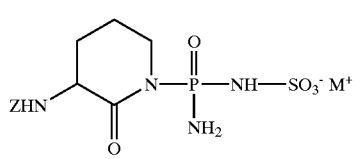

(VIII)

In the formula, Z is the same amino group-protecting group as in the general formula (VI), and $M^+$ is a monovalent cation such as $Li^+$, $Na^+$, $K^+$, $R_3NH^+$, $R_2NH_2^+$, $RNH_3^+$ and pyridinium, in which R is a lower alkyl group substituted or unsubstituted with an aryl group such as phenyl and naphthyl. The solvent includes an aprotic solvent such as 1,2-dichloroethane, chloroform, methylene chloride, tetrahydrofuran, dioxane, DMF, dimethylacetamide, hexamethylphosphoramide (HMPA), N-methylpyrrolidone and acetonitrile. Preferred is dimethylformamide (DMF). The compound of the general formula (VIII) is a mixture of two diastereoisomers in relation to the asymmetric carbon at a joint of the protected amino group, because asymmetry is newly generated at the phosphorus atom. These isomers can be separated from each other in a manner such that an aqueous solution of sodium hydroxide, sodium carbonate, sodium hydrogen carbonate or the like is added to the above-mentioned reaction mixture to perform neutralization, thereby obtaining a sodium salt thereof, or an aqueous solution of potassium hydroxide, potassium carbonate, potassium hydrogen carbonate or the like is added to the above-mentioned reaction mixture to perform neutralization, thereby obtaining a potassium salt thereof, which salt is then subjected to chromatography. In the chromatography, SEPHADEX LH 20, anion exchange resins, polystyrene based adsorption resins (DIAION HP 20, AMBERLITE XAD 2 and the like), and reversed phase silica gels (ODS silica gel, octylsilica gel and the like) can be used.

In either case, the chromatographic fractionation can be carried out while confirming the separation by means of a high-performance liquid chromatography. The confirmation of separation can be carried out by monitoring an ultraviolet absorption with use of, for example, ODS silica gel column and a buffer solution or a mixture of an aqueous acid solution with methanol or acetonitrile as an eluent.

For example, it has been confirmed that with respect to a sodium salt of a compound of the general formula (VIII), wherein Z is benzyloxycarbonyl, when subjected to elution by means of chromatography using DIAION HP 20 as a packing according to a linear concentration gradient method wherein a constitution ratio of eluant goes from water to methanol, both isomers of the compound of the general formula (VIII) in each sodium salt can be separated from each other at a methanol concentration between 20 and 60%, though the separation is not complete.

Both stereo isomers of the compound of the general formula (VIII) are subjected to removal of the amino group-protecting group Z according to a conventional method, thereby obtaining a compound of the formula (V). Any means of removing the protecting group different depending upon the kind of the protecting group is known in the art. For example, a benzyloxycarbonyl group, a t-butoxycarbonyl group, a p-methoxybenzyloxycarbonyl group and a phthaloyl group can be removed by means of a catalytic reduction, an acid, a catalytic reduction or an acid, and a hydrazine decomposition, respectively.

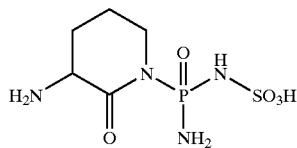

(V)

Among the thus obtained stereo isomers of the compound of the formula (V), a substance has been found to perfectly agree with the above-mentioned sulphostin obtained by the cultivation of microorganisms on the basis of behavior thereof in chromatography, physico-chemical properties thereof and enzyme inhibition activities mentioned below, which substance was obtained by subjecting the compound of the formula (VIII) having a benzyloxycarbonyl group to chromatography using DIAION HP 20, and further subjecting a later eluate to catalytic reduction to remove the benzyloxycarbonyl group. Thereby, a synthetic chemical process for producing sulphostin in accordance with the present invention has been attained.

In a manner similar to that in the synthesis of sulphostin mentioned above, two stereo isomers of the sulphostin have been obtained from D-ornithine.

With respect to a compound of the general formula (IV) wherein n is 0, namely a 4-membered compound, it can be obtained by using known 4-(carbobenzoxyamino-2-azetidinone) as it is.

Furthermore, compounds of general formulas (IX), (X), (XI) and (XII) have been obtained similarly from 2-aminocaprolactam and methyl L-2,4-diaminobutyrate obtained through Hofmann degradation of methyl N-protected glutamate.

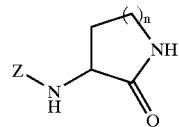

(IX)

In the formula, n is 0, 1 or 3, and Z is the same amino group-protecting group as in the general formula (VI).

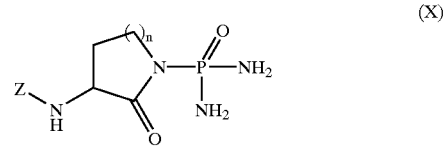

(X)

In the formula, n is 0, 1 or 3, and Z is the same amino group-protecting group as in the general formula (VI).

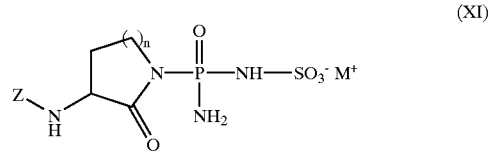

(XI)

In the formula, n is 0, 1 or 3, Z is the same amino group-protecting group as in the general formula (VI), and $M^+$ is the same monovalent cation as in the general formula (VIII).

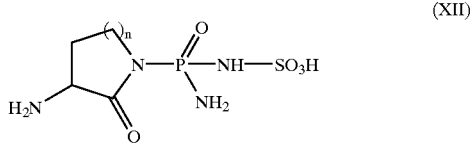

(XII)

In the formula, n is 0, 1 or 3.

Since the compound of the general formula (XI) has been found to be a mixture of diastereoisomers like in the case of sulphostin, respective isomers have been chromatographically separated. The compound of the general formula (XI) separated has been subjected to removal of the protecting group, thereby obtaining a stereo isomer of the compound of the general formula (XII).

The present invention is explained in detail with reference to Examples and Test Example, which are not intended to limit the scope of the present invention. Hereinafter, the "room temperature" is of from 10 to 30° C.

EXAMPLE 1

3(S)-Benzyloxycarbonylamino-2-piperidone (Compound 1)

Thionyl chloride (69.2 ml, 0.9487 mol) was added to methanol (1.2 l) under ice cooling, and the mixture was stirred for 20 minutes. Successively, each of L-ornithine hydrochloride (80.00 g, 0.4744 mol) divided into 4 portions was added thereto, and the resulting mixture was stirred at that temperature for 3 hours and further stirred at room temperature for 19 hours.

The reaction liquid was concentrated under reduced pressure and then crystallized from ether-hexane, followed by washing with ether, thereby obtaining colorless crystals of L-ornithine methyl ester dihydrochloride.

The obtained colorless crystals were dissolved in water (1 l), each of sodium hydrogen carbonate (119.56 g, 1.4232 mol) divided into several portions was added thereto under ice cooling, and the mixture was stirred at room temperature for 15 hours.

Successively, after adding THF (0.5 l) and sodium hydrogen carbonate (59.78 g, 0.7116 mol) to the reaction liquid, benzyloxycarbonyl chloride (81.3 ml, 0.5695 mol) was added thereto under ice cooling, and the mixture was stirred at room temperature for 18 hours.

The reaction liquid separating into two layers was subjected to separation, and the separated aqueous layer was neutralized with hydrochloric acid, followed by extraction with chloroform. A combination of the extract with the organic layer separated above was washed with an aqueous solution saturated with sodium chloride, and dried on anhydrous sodium sulfate, and then the solvent was evaporated. Ether was added to the residue to perform crystallization, followed by washing with ether, thereby obtaining a crude crystal (105.60 g). A combination of the crystallization mother liquor and the washing liquid of ether was purified by means of silica gel chromatography (chloroform: ethyl acetate=10:1~2:1), thereby obtaining another crude crystal (2.20 g). Both crude crystals were combined, followed by re-crystallization (chloroform-ehter), thereby obtaining the desired compound (106.34 g).

$^1$H-NMR (CDCl$_3$); δ: 7.28~7.38 (5H, m), 6.36 (1H, br s), 5.79 (1H, br s), 5.11 (2H, s), 4.06~4.12 (1H, m), 3.27~3.33 (2H, m), 2.46~2.53 (1H, m), 1.82~1.95 (2H, m), 1.61 (1H, tdd, J=11.7, 12.7, 5.4 Hz). MS (FAB, POS); m/Z: 249 [M+H]$^+$, 271 [M+Na]$^+$.

EXAMPLE 2

3(S)-Benzyloxycarbonylamino-1-diaminophosphinyl-2-piperidone (Compound 2)

The compound 1 obtained above (40.00 g, 0.1611 mol) was dissolved in anhydrous THF (450 ml) under a nitrogen stream, and after cooling the resulting solution at an external temperature of −78° C., a hexane solution of n-butyllithium (1.54 M, 99 ml, 0.1525 mol) was gradually added thereto. The mixture was stirred for 45 minutes. Then, an anhydrous THF (20 ml) solution of phosphoryl chloride (15.0 ml, 0.1609 mol) was added thereto, and the mixture was stirred at that temperature for 1.5 hours and additionally stirred at room temperature for 1 hour. After cooling at an external temperature of −78° C. again, liquefied ammonia (15 ml, 0.6791 mol) was added thereto, and the mixture was stirred for 5 minutes.

To the reaction liquid was added an aqueous solution saturated with sodium chloride (about 500 ml). The reaction liquid of two layers was subjected to separation, and the aqueous layer was subjected to extraction with chloroform. A combination of the extract and the organic layer separated above was washed with an aqueous solution saturated with sodium chloride and dried on anhydrous sodium sulfate, and the solvent was evaporated. The residue was crystallized from chloroform-ether, thereby obtaining the desired compound (19.63 g).

$^1$H-NMR (DMSO-D$_6$); δ: 7.28~7.41 (6H, m), 5.00 (2H, s), 4.19 (2H, br s), 4.14 (2H, br s), 4.06~4.12 (1H, m), 3.55~3.61 (1H, m), 3.43~3.48 (1H, m), 1.98~2.03 (1H, m), 1.73~1.78 (2H, m), 1.58~1.66 (1H, m). MS (FAB, POS); m/Z: 327 [M+H]$^+$.

EXAMPLE 3

(S)-Phenethylamine Salt of 3(S)-Benzyloxycarbonylamino-1-((S*)-amino (sulfoamino)phosphinyl)-2-piperidone (Compound 3) and (S)-Phenethylamine Salt of 3(S)-Benzyloxycarbonylamino-1-((R*)-amino (sulfoamino)-phosphinyl)-2-piperidone (Compound 4)

To a suspension of the compound (2) obtained above (5.00 g, 15.32 mmol) and DMF (40 ml) was added sulfur trioxide-pyridine complex (3.17 g, 19.92 mmol), and the mixture was stirred at an external temperature of 6 to 8° C. for 18 hours.

Water (250 ml) and sodium hydrogen carbonate (3.22 g, 38.33 mmol) were added to the resulting reaction liquid. The aqueous layer was washed with chloroform, and thereafter subjected to concentration gradient elution with water-methanol using DIAION HP-20SS column, thereby obtaining a former eluate of an isomer (1.04 g, tentatively called sodium salt of 3(S)-benzyloxycarbonylamino-1-((S*)-amino(sulfoamino)-phosphinyl)-2-piperidone), and a later eluate of an isomer (0.80 g, tentatively called sodium salt of 3(S)-benzyloxycarbonylamino-1-((R*)-amino(sulfoamino)-phosphinyl)-2-piperidone). Successively, (S)-phenethylamine hydrochloride (0.60 g) was added to each of the diastereomers, followed by purification again using DIAION HP-20SS column, thereby obtaining the desired compound 3 (0.81 g) and compound 4 (0.88 g).

Compound 3
$^1$H-NMR(CD$_3$OD); δ: 7.26~7.47 (10H, m), 5.06 (2H, s), 4.46 (1H, q, J=6.8 Hz), 4.20~4.24 (1H, m), 3.73~3.80 (1H, m), 3.57~3.62 (1H, m), 2.16~2.23 (1H, m), 1.85~1.96 (2H, m), 1.71~1.81 (1H, m), 1.62 (3H, d, J=6.8 Hz).

Compound 4
$^1$H-NMR (CD$_3$OD); δ: 7.26~7.45 (10H, m), 5.09 (2H, s), 4.47 (1H, q, J=6.8 Hz), 4.20 (1H, dd, J=6.3, 11.2 Hz), 3.82~3.89 (1H, m), 3.54~3.61 (1H, m), 2.04~2.19 (2H, m), 1.72~1.85 (2H, m), 1.62 (3H, d, J=6.8 Hz).

EXAMPLE 4

3(S)-Amino-1-((S*)-amino(sulfoamino)phosphinyl)-2-piperidone (Compound 5)

To a solution obtained by dissolving the compound 3 obtained above (814.5 mg, 1.5440 mmol) in methanol (18 ml) and water (2 ml), palladium black (80 mg) was added, and the mixture was stirred at room temperature for 17 hours under a hydrogen stream.

After adding water (10 ml) to the resulting reaction liquid, removal of the catalyst by filtration and concentration of the solvent in vacuo were carried out, and the residue was subjected to purification using DIAION HP-20SS. Thereafter, re-crystallization (water-ethanol) gave the desired compound (270.0 mg).

$^1$H-NMR (D$_2$O); δ: 4.15 (1H, dd, J=6.8, 11.7 Hz), 3.62~3.77 (2H, m), 2.43 (1H, td, J=12.2, 5.4 Hz), 1.98~2.12 (2H, m), 1.93 (1H, tdd, J=12.2, 9.5, 6.7 Hz). $^{13}$C-NMR (D$_2$O); δ: 172.3, 51.3, 45.7, 24.6, 20.9; $^{31}$P-NMR (D$_2$O); δ: 6.31; MS (FAB, POS); m/Z: 193 [M-SO$_3$+H]$^+$, 273 [M+H]$^+$. MS (FAB, NEG); m/Z: 271 [M−H]$^-$. [α]$_D^{22}$+43.8° (water, c=0.5).

EXAMPLE 5

3(S)-Amino-1-((R*)-amino(sulfoamino)phosphinyl)-2-piperidone (Compound 6)

To a solution obtained by dissolving the compound 4 obtained above (3379.8 mg) in methanol (30 ml) and water (30 ml), palladium black (365 mg) was added. Using a PARR low-pressure catalytic reduction apparatus, the mixture was stirred at room temperature for 1 hour under a hydrogen pressure of 43 psi.

The catalyst was removed from the reaction liquid by filtration, and thereafter the filtrate was passed through a column packed with a cation exchange resin, IRC 50 (H Type), (50 ml). The liquid positive to a ninhydrin reaction and passed through the column and the liquid of water-washing were collected, followed by subjecting to concentration of the solvent in vacuo. The residue was re-crystallized from water-ethanol, thereby obtaining the desired compound (1625.6 mg). The resulting substance was found to agree with natural sulphostin in their physico-chemical properties and enzyme inhibition activities.

$^1$H-NMR (D$_2$O); δ: 4.18 (1H, dd, J=6.8, 12.0 Hz), 3.82 (1H, tdd, J=5.1, 7.3, 13.0 Hz), 3.70 (1H, tdd, J=5.1, 6.7, 13.0 Hz), 2.39~2.44 (1H, m), 2.10~2.28 (1H, m), 1.89~2.03 (2H, m). $^{13}$C-NMR (D$_2$O); δ: 172.4, 51.3, 45.4, 24.2, 20.5; $^{31}$P-NMR (D$_2$O); δ: 6.01; MS (FAB, POS); m/Z: 193 [M-SO$_3$+H]$^+$, 273 [M+H]$^+$. MS (FAB, NEG); m/Z:271 [M-H]$^-$. $[α]_D^{28}$ −21.5° (water, c=0.5).

EXAMPLE 6

3(R)-Amino-1-((R*)-amino(sulfoamino) phosphinyl)-2-piperidone (Compound 7) and 3 (R)-amino-1-((S*)-amino(sulfoamino)phosphinyl)-2-piperidone (Compound 8)

Example 1 to Example 4 were repeated, except that D-ornithine hydrochloride was used as a material and (R)-phenethylamine salt was generated on the way, thereby performing the desired synthesis.

Compound 7

$^1$H-NMR (D$_2$O); δ: 4.13 (1H, dd, J=6.8, 11.7 Hz), 3.67~3.72 (2H, m), 2.42 (1H, td, J=12.2, 5.3 Hz), 1.96~2.11 (2H, m), 1.90 (1H, tdd, J=12.2, 9.3, 6.4 Hz). MS (FAB, POS); m/Z: 193 [M-SO$_3$+H]$^+$, 273 [M+H]$^+$. $[α]_D^{22}$ −43.6° (water, c=0.5).

Compound 8

$^1$H-NMR (D$_2$O); δ: 4.13 (1H, dd, J=6.8, 11.7 Hz), 3.78 (1H, tdd, J=5.3, 7.4, 13.0 Hz), 3.64 (1H, tdd, J=4.9, 7.4, 13.0 Hz), 2.34~2.43 (1H, m), 2.05~2.16 (1H, m), 1.84~2.00 (2H, m). MS (FAB, POS); m/Z: 193 [M-SO$_3$+H]$^+$, 273 [M+H]$^+$. $[α]_D^{23}$ +21.5 (water, c=0.5).

EXAMPLE 7

3(S)-Benzyloxycarbonylamino-2-caprolactam (Compound 9)

To a solution obtained by dissolving 3(S)-amino-2-caprolactam (5.00 g, 39.01 mmol) in THF (20 ml) and water (40 ml), sodium hydrogen carbonate (4.92 g, 58.56 mol) and benzyloxycarbonyl chloride (5.57 ml, 39.01 mmol) were added under ice cooling, and the mixture was stirred at room temperature for 18 hours.

The reaction liquid was concentrated in vacuo, thereafter water was added thereto, and crystals precipitated were collected by filtration. After washing with ether, the crystals were dissolved in chloroform, followed by drying on anhydrous sodium sulfate. Evaporation of the solvent and re-crystallization (chloroform-ether) gave the desired compound (5.23 g).

$^1$H-NMR (CDCl$_3$); δ: 7.26~7.36 (5H, m), 6.14~6.24 (2H, m), 5.10 (2H, d, J=2.8 Hz), 4.34 (1H, ddd, J=1.6, 6.8, 13.6 Hz), 3.19~3.31 (2H, m), 2.09~2.15 (1H, m), 1.98~2.05 (1H, m), 1.73~1.87 (2H, m), 1.48~1.58 (1H, m), 1.33~1.44 (1H, m).

EXAMPLE 8

3(S)-Benzyloxycarbonylamino-1-diaminophosphinyl-2-caprolactam (Compound 10)

The compound 9 obtained above (4.00 g, 15.25 mmol) was dissolved in anhydrous THF (120 ml) under a nitrogen stream, and after cooling the resulting solution at an external temperature of −78° C., a hexane solution of n-butyllithium (1.55 M, 8.9 ml, 13.80 mmol) was gradually added thereto. The mixture was stirred for 30 minutes. Then, an anhydrous THF (10 ml) solution of phosphoryl chloride (2.57 g, 16.76 mmol) was added thereto, and the mixture was stirred at that temperature for 2 hours and additionally stirred at room temperature for 30 minutes. After cooling at an external temperature of −78° C. again, liquefied ammonia (2 ml, 90.55 mmol) was added thereto, and the mixture was stirred for 5 minutes.

An aqueous solution saturated with sodium chloride was added to the reaction liquid to separate into an aqueous layer and an organic layer. The aqueous layer was subjected to extraction with chloroform. A combination of the extract and the organic layer separated above was washed with an aqueous solution saturated with sodium chloride and dried on anhydrous sodium sulfate, and the solvent was evaporated. The residue was purified by means of silica gel chromatography (chloroform:methanol=29:1~14:1), and the obtained crystal was washed with chloroform-ether, thereby obtaining the desired compound (1.55 g).

$^1$H-NMR (DMSO-D$_6$); δ: 7.25~7.38 (6H, m), 5.01 (2H, d, J=4.8 Hz), 4.39~4.45 (1H, m), 4.16 (2H, br s), 4.11 (2H, br s), 3.20~3.30 (2H, m), 1.48~1.80 (5H, m), 1.33~1.43 (1H, m).

EXAMPLE 9

(S)-Phenethylamine Salt of 3(S)-benzyloxycarbonylamino-1-((R*)-amino (sulfoamino)phosphinyl)-2-caprolactam (Compound 11) and (S)-phenethylamine Salt of 3(S)-Benzyloxycarbonylamino-1-((S*)-amino (sulfoamino)-phosphinyl)-2-caprolactam (Compound 12)

To a suspension of the compound 10 obtained above (800.4 mg, 2.3519 mmol) and DMF (8 ml), sulfur trioxide-pyridine complex (561.5 mg, 2.9291 mmol) was added, and the mixture was stirred at an external temperature of 6 to 8° C. for 15 hours.

Water (50 ml) and sodium hydrogen carbonate (600 mg, 7.1420 mmol) were added to the resulting reaction liquid. After washing the mixture with chloroform, separation and purification were carried out using DIAION HP-20SS, thereby obtaining a former eluate of an isomer (tentatively called sodium salt of 3(S)-benzyloxycarbonylamino-1-((R*)-amino(sulfoamino)-phosphinyl)-2-caprolactam, and a later eluate of an isomer (tentatively called sodium salt of 3(S)-benzyloxycarbonylamino-1-((S*)-amino(sulfoamino)-phosphinyl)-2-caprolactam. Successively, (S)-phenethylamine hydrochloride (50 mg) was added to each of the diastereomers, followed by purification again using DIAION HP-20SS, thereby obtaining the desired compound 11 (69.8 mg) and compound 12 (30.0 mg).

Compound 11

$^1$H-NMR (CD$_3$OD); δ: 7.22~7.42 (10H, m), 5.02~5.06 (2H, m), 4.42 (1H, q, J=6.8 Hz), 4.13~4.21 (1H, m), 3.25~3.35 (2H, m), 1.85~1.98 (3H, m), 1.75~1.82 (1H, m), 1.65~1.70 (2H, m), 1.58 (3H, dd, J=3.4, 6.8 Hz).

Compound 12

$^1$H-NMR (CD$_3$OD); δ: 7.22~7.42 (10H, m), 5.03 (2H, s), 4.41 (1H, q, J=6.8 Hz), 4.14~4.22 (1H, m), 3.27~3.32 (2H, m), 1.71~1.96 (4H, m), 1.54~1.64 (1H, m), 1.58 (3H, d, J=6.8 Hz), 1.38~1.48 (1H, m).

EXAMPLE 10

3(S)-Amino-1-((R*)-amino(sulfoamino phosphinyl)-2-caprolactam (Compound 13)

To a solution obtained by dissolving the compound 11 obtained above (69.3 mg, 0.1280 mmol) in methanol (2 ml) and water (2 ml), palladium black (6.9 mg) was added, and the mixture was stirred at room temperature for 3 hours under a hydrogen stream.

Removal of the catalyst in the reaction liquid by filtration and concentration of the solvent in vacuo were carried out. The residue was subjected to purification using DIAION HP-20SS. Thereafter, re-crystallization (water-ethanol) gave the desired compound (22.0 mg).

$^1$H-NMR (D$_2$O); δ: 4.34 (1H, dd, J=3.2, 10.0 Hz), 3.99 (1H, ddd, J=6.2, 11.0, 16.0Hz), 3.26 (1H, td, J=11.0, 16.0 Hz), 1.82~1.92 (3H, m), 1.73~1.79 (1H, m), 1.60~1.70 (2H, m). MS (FAB, POS); m/Z: 207 [M-SO$_3$+H]$^+$, 287 [M+H]$^+$.

EXAMPLE 11

3(S)-Amino-1-((S*)-amino(sulfoamino)phosphinyl)-2-caprolactam (Compound 14)

To a solution obtained by dissolving the compound 12 obtained above (30.0 mg, 0.0554 mmol) in methanol (1 ml) and water (0.5 ml), palladium black (3 mg) was added, and the mixture was stirred at room temperature for 3 hours under a hydrogen stream.

Removal of the catalyst in the reaction liquid by filtration and concentration of the solvent in vacuo were carried out. The residue was subjected to purification using DIAION HP-20SS. Thereafter, re-crystallization (water-ethanol) gave the desired compound (12.5 mg).

$^1$H-NMR (D$_2$O); δ: 4.37 (1H, d, J=11.2 Hz), 4.00 (1H, ddd, J=5.4, 10.5, 15.6 Hz), 3.24 (1H, td, J=11.2, 15.6 Hz), 1.60~1.95 (5H, m), 1.30~1.40 (1H, m). MS (FAB, POS); m/Z: 207 [M-SO$_3$+H]$^+$, 287 [M+H]$^+$.

EXAMPLE 12

Methyl L-Benzyloxycarbonylglutamate (Compound 15)

To a solution obtained by dissolving L-benzyloxycarbonylglutamine (8.00 g, 28.54 mmol) in DMF (80 ml), sodium hydrogen carbonate (4.80 g, 57.14 mol) and methyl iodide (4.44 ml, 71.32 mmol) were added, and the mixture was stirred at room temperature for 22 hours.

The reaction liquid was mixed with water, followed by extraction with ethyl acetate. The ethyl acetate layer was washed with a 10% sodium thiosulfate aqueous solution and an aqueous solution saturated with sodium chloride and then dried on anhydrous sodium sulfate, and the solvent was removed by distillation. The residue was washed with ethyl acetate-ether, thereby obtaining the desired compound (6.60 g).

$^1$H-NMR (CD$_3$OD); δ: 7.26~7.37 (5H, m), 5.09 (2H, s), 4.21 (1H, dd, J=5.2, 9.2 Hz), 3.72 (3H, s), 2.31 (2H, t, J=7.8 Hz), 2.10~2.19 (1H, m), 1.88~1.97 (1H, m).

EXAMPLE 13

3(S)-Benzyloxycarbonylamino-2-pyrrolidone (Compound 16)

To a suspension of bis(trifluoroacetoxy)-iodobenzene (10.45 g, 24.30 mmol), acetonitrile (50 ml), water (50 ml) and pyridine (3.02 ml, 37.34 mmol), the compound 15 obtained above (5.50 g, 18.69 mmol) was added, and the mixture was stirred at room temperature for 4 hours.

The reaction liquid was concentrated in vacuo and mixed with water, followed by extraction with ethyl acetate. The ethyl acetate layer was washed with an aqueous solution saturated with sodium chloride and then dried on anhydrous sodium sulfate, and the solvent was removed by distillation.

To a solution obtained by dissolving the residue in chloroform (100 ml), a sodium hydrogen carbonate aqueous solution (5 g/100 ml) was added, and the mixture was stirred at room temperature for 17 hours.

The reaction liquid was separated into an aqueous layer and a chloroform layer, and the aqueous layer was extracted with chloroform. The combined chloroform layer was washed with an aqueous solution saturated with sodium chloride and then dried on anhydrous sodium sulfate, and thereafter the solvent was removed by distillation. The residue was washed with ether, thereby obtaining the desired compound (2.41 g).

$^1$H-NMR (CDCl$_3$); δ: 7.28~7.38 (5H, m), 6.49 (1H, br s), 5.49 (1H, br d, J=4.9 Hz), 5.11 (2H, s), 4.21~4.27 (1H, m), 3.29~3.38 (2H, m), 2.65~2.73 (1H, m), 1.98 (1H, qd, J=9.8, 12.2 Hz).

EXAMPLE 14

3(S)-Benzyloxycarbonylamino-1-diaminophophinyl-2-pyrrolidone (Compound 17)

To a solution obtained by dissolving the compound 16 obtained above (3.00 g, 12.81 mmol) in anhydrous THF (210 ml), a hexane solution of n-butyllithium (1.54 M, 7.9 ml, 12.17 mmol) was gradually added at an external temperature of −78° C. under a nitrogen stream, and the mixture was stirred for 45 minutes. Successively, an anhydrous THF (4 ml) solution of phosphoryl chloride (1.96 g, 12.78 mmol) was added thereto, and the mixture was stirred at that temperature for 50 minutes, and additionally stirred at room temperature for 1 hour. The reaction liquid was again cooled at an external temperature of −78° C., and liquefied ammonia (2.5 ml, 113 mmol) was added thereto. The mixture was stirred for 5 minutes.

The solvent was removed by distillation in vacuo, and a sodium chloride aqueous solution was added to the residue. The aqueous layer was washed with hexane and chloroform, and thereafter subjected to purification using DIAION HP-20SS. The obtained crystal was washed with chloroform-ether, thereby obtaining the desired compound (1.83 g).

$^1$H-NMR (CD$_3$OD); δ: 7.26~7.37 (5H, m), 5.01 (2H, s), 4.35 (1H, dd, J=8.4, 11.2 Hz), 3.72 (1H, dd, J=8.8, 10.0 Hz), 3.53 (1H, td, J=10.0, 6.4 Hz), 2.37~2.44 (1H, m), 1.95~2.06 (1H, m). MS (FAB, POS); m/Z: 313 [M+H]$^+$, 335 [M+Na]$^+$.

EXAMPLE 15

(S)-Phenethylamine Salt of 3(S)-Benzyloxycarbonylamino-1-((S*)-amino(sulfoamino)phosphinyl)-2-pyrolidone (Compound 18) and (S)-Phenethylamine Salt of 3(S)-Benzyloxycarbonylamino-1-((R*)-amino(sulfoamino)-phosphinyl)-2-pyrrolidone (Compound 19)

To a suspension of the compound 17 obtained above (2.00 g, 6.40 mmol) and DMF (30 ml), sulfur trioxide-pyridine complex (2.04 g, 12.82 mmol) was added, and the mixture was stirred at an external temperature of 6 to 8° C. for 4 hours.

Water (50 ml) and sodium hydrogen carbonate (600 mg, 7.1420 mmol) were added to the resulting reaction liquid. After washing the mixture with chloroform, separation purification was carried out using DIAION HP-20SS, thereby obtaining a former eluate of an isomer (tentatively called sodium salt of 3(S)-benzyloxycarbonylamino-1-((S*)-amino(sulfoamino)-phosphinyl)-2-pyrrolidone), and a later eluate of an isomer (tentatively called sodium salt of 3(S)-benzyloxycarbonylamino-1-((R*)-amino(sulfoamino)-phosphinyl)-2-pyrrolidone). Successively, (S)-phenethylamine hydrochloride (1.00 g) was added to each of the diastereomers, followed by purification using DIAION HP-20SS and SEPHADEX LH-20, thereby obtaining the desired compound 18 (201.5 mg) and compound 19 (125.7 mg).

Compound 18

$^1$H-NMR (CD$_3$OD); 7.26~7.47 (10H, m), 5.08 (2H, s), 4.45 (1H, q, J=6.8 Hz), 4.40 (1H, dd, J=8.8, 12.0 Hz), 3.66~3.74 (2H, m), 2.36~2.43 (1H, m), 1.95~2.06 (1H, m), 1.62 (3H, d, J=6.8 Hz). MS (FAB, POS); m/Z: 313 [M-phenethylamine-SO$_3$+H]$^+$, 434 [M-SO$_3$+H]$^+$, 635 [M+phenethylamine+H]$^+$. MS (FAB, NEG); m/Z: 391 [M-phenethylamine-H]$^-$.

Compound 19

$^1$H-NMR (CDCl$_3$+CD$_3$OD); 7.30~7.43 (10H, m), 5.09 (2H, s), 4.48 (1H, dd, J=8.3, 11.2 Hz), 4.41 (1H, q, J=6.8 Hz), 3.75~3.80 (1H, m), 3.51 (1H, td, 10.3, 3.9 Hz), 2.39~2.46 (1H, m), 1.95~2.06 (1H, m), 1.63 (3H, d, J=6.8 Hz). MS (FAB, POS); m/Z: 313 [M-phenethylamine-SO$_3$+H]$^+$, 434 [M-SO$_3$+H]$^+$, 514 [M+H]$^+$, 635 [M+phenethylamine+H]$^+$. MS (FAB, NEG); m/Z: 391 [M-phenethylamine-H]$^-$.

EXAMPLE 16

3(S)-Amino-1-((S*)-amino(sulfoamino)phosphinyl)-2-pyrrolidone (Compound 20)

To a solution obtained by dissolving the compound 18 obtained above (179.5 mg, 0.3496 mmol) in methanol (3 ml) and water (3 ml), palladium black (18 mg) was added, and the mixture was stirred at room temperature for 1 hour under a hydrogen stream.

Removal of the catalyst in the reaction liquid by filtration and concentration of the solvent in vacuo were carried out. The residue was subjected to purification using DIAION HP-20SS. Thereafter, re-crystallization (water-ethanol) gave the desired compound (73.0 mg).

$^1$H-NMR (D$_2$O); 4.16 (1H, dd, J=8.8, 12.2 Hz), 3.71~3.76 (1H, m), 3.61 (1H, td, 10.3, 6.3 Hz), 2.49~2.56 (1H, m), 2.06 (1H, tdd, J=12.2, 9.3, 10.8 Hz). MS (FAB, POS); m/Z: 179 [M-SO$_3$+H]$^+$, 259 [M+H]$^+$.

EXAMPLE 17

3(S)-Amino-1-((R*)-amino(sulfoamino)phosphinyl)-2-pyrrolidone (Compound 21)

To a solution obtained by dissolving the compound 19 obtained above (111.7 mg, 0.2175 mmol) in methanol (3 ml) and water (3 ml), palladium black (11 mg) was added, and the mixture was stirred at room temperature for 1 hour under a hydrogen stream.

Removal of the catalyst in the reaction liquid by filtration and concentration of the solvent in vacuo were carried out. The residue was subjected to purification using DIAION HP-20SS. Thereafter, re-crystallization (water-ethanol) gave the desired compound (50.5 mg).

$^1$H-NMR (D$_2$O); 4.16 (1H, dd, J=8.8, 11.7 Hz), 3.73~3.78 (1H, m), 3.56 (1H, td, 10.3, 6.3 Hz), 2.47~2.54 (1H, m), 2.06 (1H, tdd, J=12.2, 9.3, 10.3 Hz). MS (FAB, POS); m/Z:179 [M-SO$_3$+H]$^+$, 259 [M+H]$^+$.

TEST EXAMPLE 1

Measurement of Dipeptidylpeptidase IV Inhibiting Activity

Water was added to a mixture of 0.025 ml of 3.2 mM glycyl prolyl β-naphthylamide (BACHEM, Switzerland), 0.1 ml of 0.1 M tris-maleic acid buffer solution (pH 7.2) and a compound shown in Table 1, so that a final volume was adjusted to 0.2 ml. The resulting mixed solution was warmed at 37° C. for 10 minutes, and 0.025 ml of a dipeptidylpeptidase IV solution partially purified through ammonium sulfate fractionation of a homogenate obtained from a kidney of a rat was added thereto. Then, the reaction was continued at 37° C. for 1 hour. Thereafter, 0.1 ml of 0.5 M sodium citrate buffer solution (pH 3.78) containing 10% of polyoxyethylene (20) sorbitan monolaurate and 0.2% of Fast Garnet GBC salt (Sigma, USA) was added thereto to discontinue the reaction, and then absorbance (a) at 525 nm was measured. At the same time, a blank test was conducted to measure absorbance (b) of the buffer solution containing no specimen. A dipeptidylpeptidase IV inhibition percent was calculated from the expression: [(b−a)/b]×100. Values of the dipeptidylpeptidase IV inhibition activity of the compounds in accordance with the present invention are as shown in Table 1.

TABLE 1

| Compound No. | IC$_{50}$ (μg/ml) |
| --- | --- |
| 5 | 100 |
| 6 | 0.0060 |
| 7 | 0.0089 |
| 8 | 24 |
| 13 | 0.0076 |
| 14 | 0.67 |
| 20 | 0.47 |
| 21 | 0.0039 |

As can be seen, the stereo isomers and analogues of sulphostin exhibited a strong inhibition activity against dipeptidylpeptidase IV.

INDUSTRIAL APPLICABILITY

The sulphostin analogue of the present invention can be used as immunomodulating agents, hormone-modulating agents, anti-HIV drugs, antiallergic drugs, anti-inflammatory drugs and antirheumatic drugs. In addition, according to the production process of the present invention, the sulphostin and analogues thereof can be obtained by a synthetic chemical means.

What is claimed is:

1. A sulphostin analogue represented by a general formula (IV′),

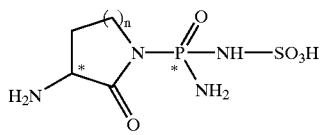

(IV′)

wherein n is an integer of from 0 to 3, provided that a case where n is 2 and steric configurations of C* and P* are S and R, respectively, is excluded, or a pharmaceutically acceptable salt thereof.

2. A process for producing sulphostin or a sulphostin analogue represented by a general formula (IV),

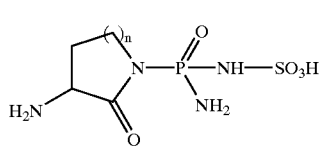

(IV)

wherein n is an integer of from 0 to 3, which comprises allowing a compound represented by a general formula (II),

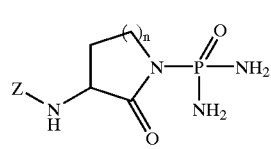

(II)

wherein n is as defined above, and Z is an amino group-protecting group, to reaction with sulfur trioxide or a complex thereof, if necessary followed by cation exchange, thereby obtaining a compound represented by a general formula (III),

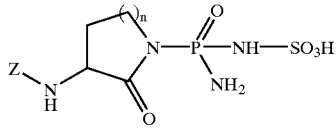

(III)

wherein n and Z are as defined above, and M is a monovalent cation, and then removing the protecting group.

3. The process according to claim 2, wherein said Z is a carbamate, amide or imide type protecting group.

4. The process according to claim 3, wherein said Z is benzyloxycarbonyl unsubstituted or substituted, or t-butoxycarbonyl.

5. The process according to any one of claims 2 to 4, wherein said M is $Li^+$, $Na^+$, $K^+$, $R_1R_2R_3NH^+$, $R_1R_2NH_2^+$, $R_1NH_3^+$ or pyridinium, in which $R_1$, $R_2$ and $R_3$ are independently of one another a $C_1$~$C_6$ lower alkyl group unsubstituted or substituted with an aryl group including phenyl or naphthyl.

6. The process according to any one of claims 2 to 5, wherein the reaction with sulfur trioxide or a complex thereof is carried out in an aprotic solvent at a temperature of from 0 to 100° C.

7. A process for producing a compound represented by a general formula (II),

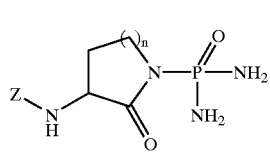

(II)

wherein n is an integer of from 0 to 3, and Z is an amino group-protecting group, which comprises allowing a compound represented by a general formula (I),

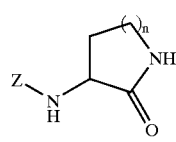

(I)

wherein n and Z are as defined above, to react with a base, followed by reaction with phosphorus oxychloride or $POX_3$ in which X is a halogen or imidazole, and further followed by reaction with ammonia in order.

8. The process according to claim 7, wherein said Z is a carbamate, amide or imide type protecting group.

9. The process according to claim 8, wherein said Z is benzyloxycarbonyl unsubstituted or substituted, or t-butoxycarbonyl.

10. The process according to any one of claims 7 to 9, wherein the reaction is carried out in an aprotic solvent at a temperature of from −80° C. to 100° C.

* * * * *